United States Patent
Unger et al.

(10) Patent No.: US 6,855,102 B2
(45) Date of Patent: Feb. 15, 2005

(54) METHOD FOR SEPARATING CELLS, ESPECIALLY PLATELETS, AND BAG ASSEMBLY THEREFOR

(75) Inventors: Peter Unger, Stockholm (SE); Eric Westberg, Lidingö (SE)

(73) Assignee: Gambro Inc, Lakewood, CO (US)

( * ) Notice: Subject to any disclaimer, the term of this patent is extended or adjusted under 35 U.S.C. 154(b) by 0 days.

(21) Appl. No.: 09/978,428

(22) Filed: Oct. 15, 2001

(65) Prior Publication Data

US 2002/0016244 A1 Feb. 7, 2002

Related U.S. Application Data

(63) Continuation of application No. 09/125,270, filed as application No. PCT/SE97/00257 on Feb. 17, 1997, now Pat. No. 6,315,706.

(30) Foreign Application Priority Data

Feb. 26, 1996 (SE) .............................................. 9600713

(51) Int. Cl.⁷ .......................... B04B 11/00; B04B 13/00
(52) U.S. Cl. ................................ 494/37; 435/2; 494/2; 494/4
(58) Field of Search .............................. 435/2; 494/2, 3, 494/4, 36, 37, 43, 44, 45

(56) References Cited

U.S. PATENT DOCUMENTS

| | | | |
|---|---|---|---|
| 3,326,458 A | * | 6/1967 | Meryman et al. |
| 3,489,145 A | | 1/1970 | Judson et al. |
| 3,519,201 A | | 7/1970 | Eisel et al. |
| 3,679,128 A | * | 7/1972 | Unger et al. |
| 3,987,961 A | | 10/1976 | Sinn et al. |
| 4,010,894 A | * | 3/1977 | Kellogg et al. |
| 4,278,202 A | | 7/1981 | Westberg |
| 4,386,730 A | | 6/1983 | Mulzet |
| 4,387,848 A | | 6/1983 | Kellogg et al. |
| 4,419,089 A | | 12/1983 | Kolobow et al. |
| 4,530,691 A | | 7/1985 | Brown |
| 4,950,401 A | * | 8/1990 | Unger et al. ............. 210/360.1 |
| 4,990,132 A | * | 2/1991 | Unger et al. .................. 494/17 |

(List continued on next page.)

FOREIGN PATENT DOCUMENTS

| | | |
|---|---|---|
| DE | 38 15 645 | 11/1989 |
| EP | 0 304 431 | 3/1989 |
| EP | 0508474 A3 | 10/1992 |
| WO | 87/06857 | 11/1987 |
| WO | WO 87/06857 | * 11/1987 |
| WO | 95/01842 | 1/1995 |
| WO | WO 95/01842 | * 1/1995 |

Primary Examiner—John Kim
(74) Attorney, Agent, or Firm—Edna M. O'Connor

(57) ABSTRACT

Method of separating cells in a centrifuge, preferably for producing platelets. A cell suspension is provided in a processing bag and is centrifuged. The cell enriched fraction is transferred to a storage bag via an outlet tube. The outlet tube is arranged with a portion thereof in a position adjacent the periphery of the centrifuge. When the enriched fraction is transferred through the outlet tube placed at the periphery of the centrifuge and during centrifugation, the outlet tube operates as a cell trap and the enriched fraction is further separated. Preferably, the cell suspension is buffy coat and the enriched fraction comprises platelets. The corresponding bag assembly comprises a processing bag intended to enclose the cell suspension. The processing bag is placed in a centrifuge rotor for separating the cells into a fraction enriched on platelets by centrifugation. An outlet tube transfers the enriched fraction to a storage bag and is placed in a position adjacent the periphery of the centrifuge rotor for further separation of the enriched fraction at transferring, during continued centrifugation, the enriched fraction through the outlet tube.

9 Claims, 7 Drawing Sheets

U.S. PATENT DOCUMENTS

| | | | | |
|---|---|---|---|---|
| 5,114,396 A | * | 5/1992 | Unger et al. | 494/37 |
| 5,116,308 A | * | 5/1992 | Hagiwara | 422/46 |
| 5,160,310 A | * | 11/1992 | Yhland | 494/45 |
| 5,316,540 A | * | 5/1994 | McMannis et al. | 494/37 |
| 5,674,173 A | * | 10/1997 | Hlavinka et al. | 494/17 |
| 5,723,050 A | * | 3/1998 | Unger et al. | 210/772 |
| 6,261,217 B1 | * | 7/2001 | Unger et al. | 494/45 |
| 6,315,706 B1 | | 11/2001 | Unger et al. | |
| 6,348,031 B1 | * | 2/2002 | Unger et al. | 494/45 |

* cited by examiner

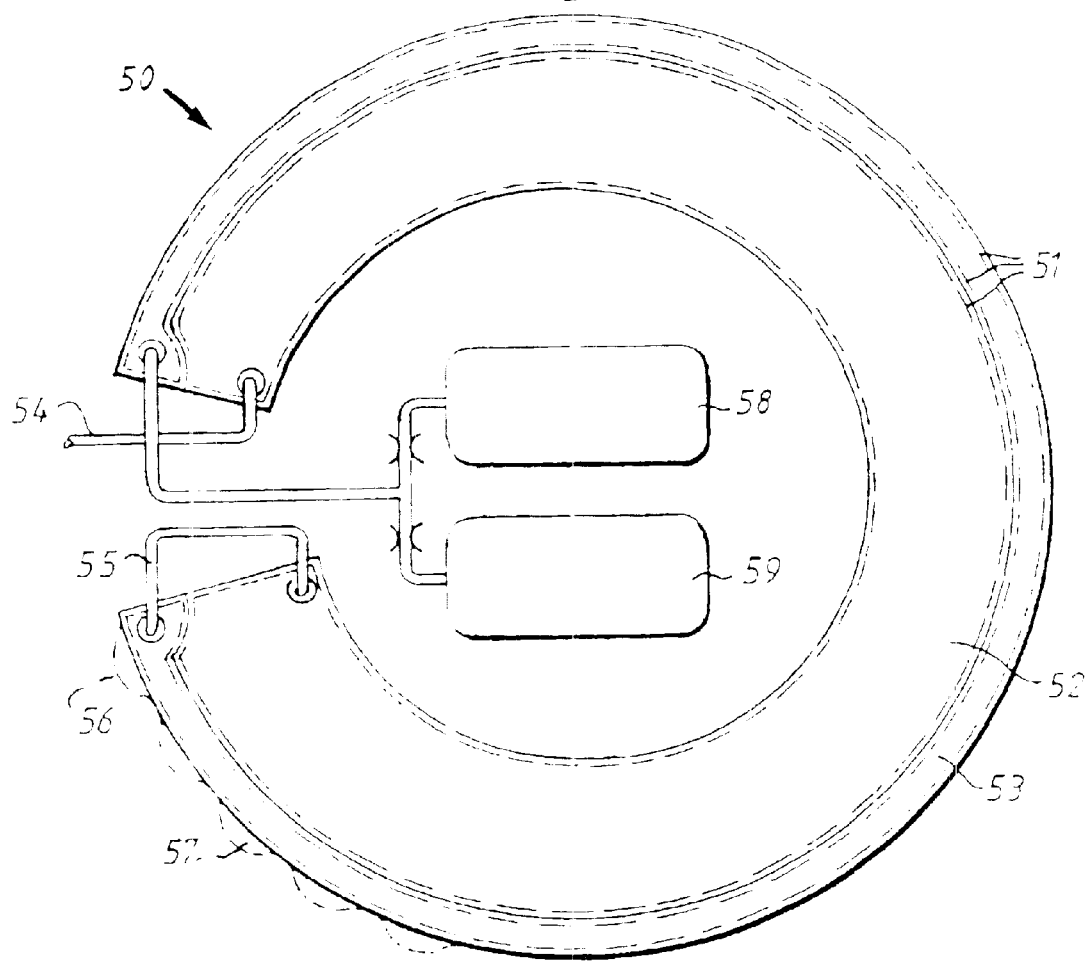
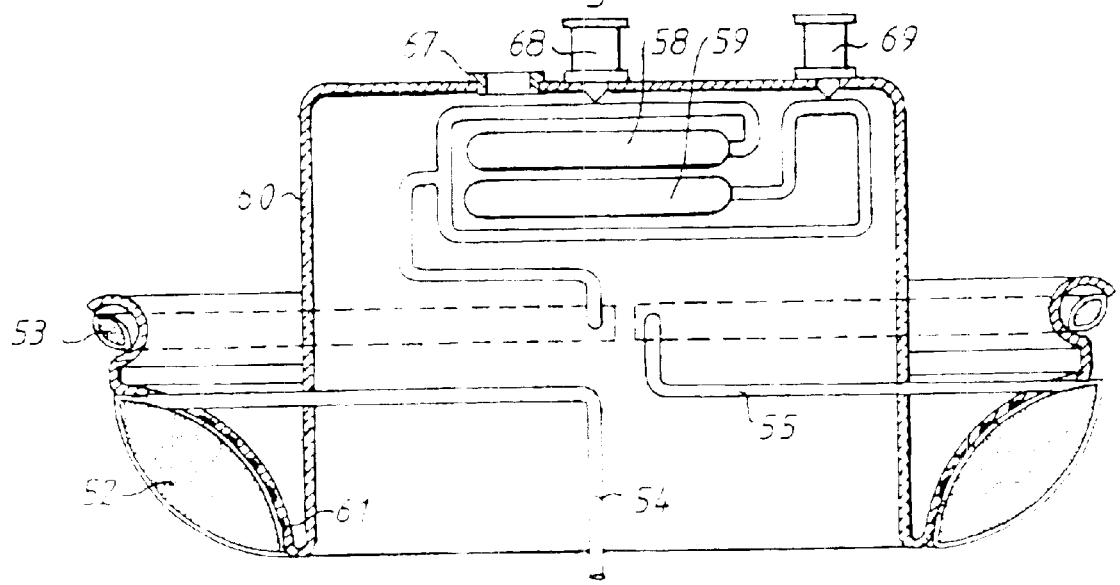

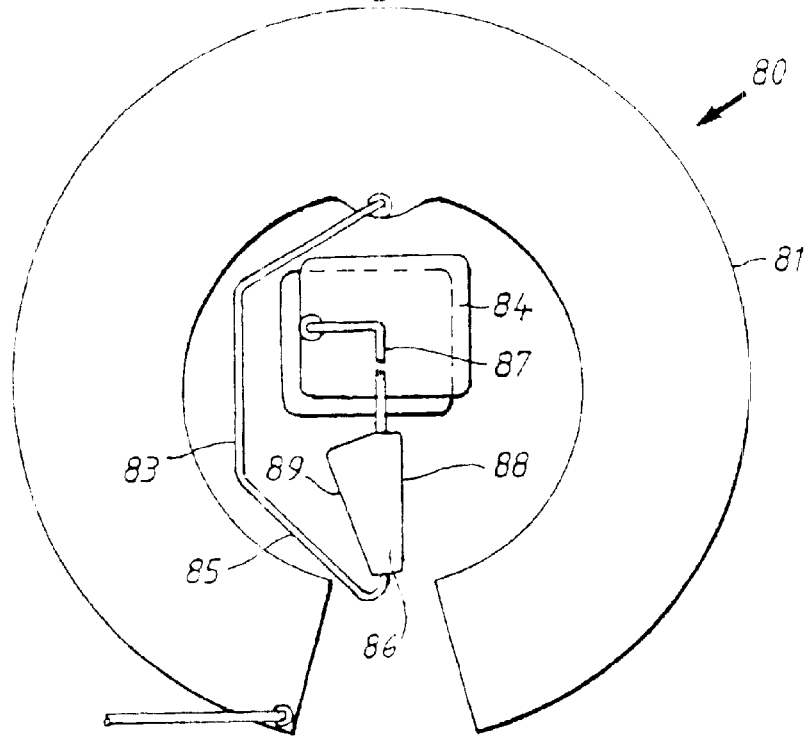
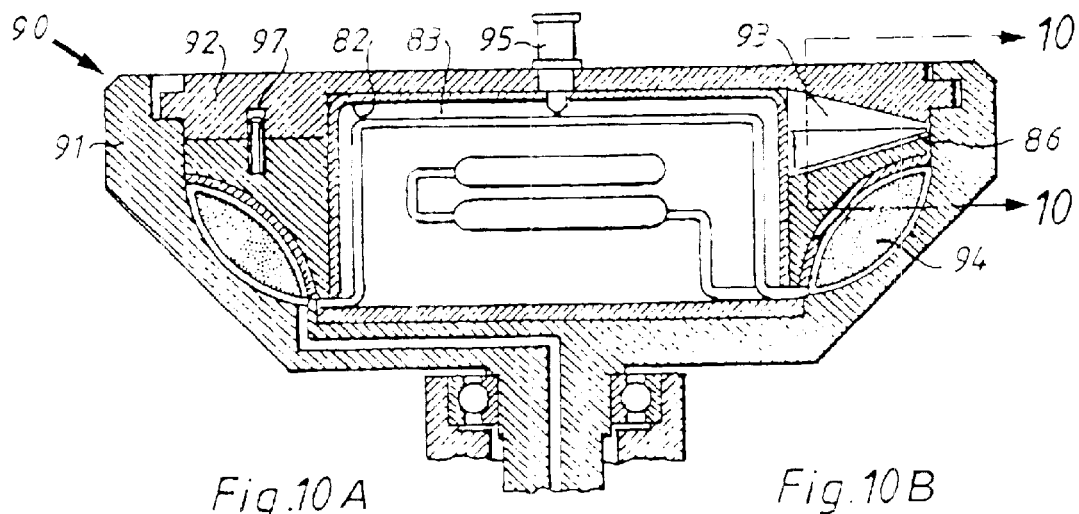
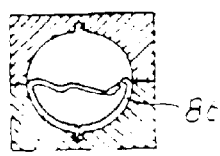 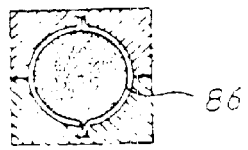

METHOD FOR SEPARATING CELLS, ESPECIALLY PLATELETS, AND BAG ASSEMBLY THEREFOR

This application is a continuation of U.S. patent application Ser. No. 09/125,270, filed Aug. 13, 1998, now U.S. Pat. No. 6,315,706 which is a PCT national filing from PCT Application No. PCT/SE97/00257 filed Feb. 17, 1997 claiming priority to Swedish Patent Application No. 9600713-3, filed Feb. 26, 1996.

AREA OF INVENTION

The present invention relates to a method and a bag assembly intended to be used in connection with the separation of cells, and specifically for the production of platelets from pooled buffy coats and in other similar areas. The invention also relates to a bag assembly therefor, which is efficient and inexpensive.

PRIOR ART

An apparatus for plasmapheresis is disclosed in EP-B1-0304 431, and comprises a round bag and a centrifuge rotor specifically adapted for performing plasmapheresis.

A further improved bag system and centrifuge separator is disclosed in WO 95/01842 and comprises a ring-shaped outer bag and a central inner bag which is formed from the central part of the ring. The outer bag is adapted to form a shortened and conical ring. The inner bag is placed in a rigid center part which prevents the radial expansion of the inner bag, but allows it to expand axially when filled with liquid. The rigid center part and the shortened outer ring are placed in a centrifuge rotor.

A container assembly for washing blood cells is disclosed in U.S. Pat. No. 5,114,396, comprising a round bag similar to the bag disclosed in EP-B1-0304 431. The container assembly comprises, in addition to a ring bag and an inner bag, further bags comprising further liquids used in the washing process. Such further bags are placed in a central rotor compartment on top of the inner bag, and are not used during the centrifugation process. When the centrifugation rotor is stopped, the liquids in said further bags are used for specific purposes.

Normally, when separating platelets from a buffy coat, the separation takes place in a centrifuge in a G-field of suitable size and during a predetermined time duration. Then, the centrifuge is stopped and the bags are removed from the centrifuge and finally extracted in a secondary step through manual proceedings. Such removal and subsequent handling will inevitably cause some mixing and deterioration of the separation. It is necessary in various forms of the prior art to include a cell filter between the centrifuge bag and the storage bag, to inhibit other cells than platelets from being transferred to the storage bag.

DISCLOSURE OF THE INVENTION

The object of the present invention is to suggest a separation process suitable for separation of platelets and similar cells from a suspension and for transportation of the separated cells to a container while maintaining a high purity and at the same time avoid using a cell filter.

A method of separation and a bag assembly for use in such a method are more clearly defined in the appended claims.

BRIEF DESCRIPTION OF THE DRAWINGS

Further features, advantages and embodiments of the invention will appear from the following detailed description of the invention with reference to the appended drawings in which:

FIG. 5 is a top view of an alternative bag assembly according to the invention.

FIG. 6 is a schematic view of an insert provided with the bag assembly according to FIG. 5.

FIG. 8 is a schematic top view of still another bag assembly according to the invention.

FIG. 9 is a cross-sectional view of a centrifuge rotor provided with the bag assembly according to FIG. 8.

FIG. 10A is a partial cross-sectional view taken according to line 10—10 in FIG. 9, showing the chamber of the cell trap in an empty condition.

FIG. 10B is also a partial cross-sectional view taken according to line 10—10 in FIG. 9, but showing the chamber of the cell trap in a filled condition occupying the entire recess.

DETAILED DESCRIPTION OF PREFERRED EMBODIMENTS

Figure 1:
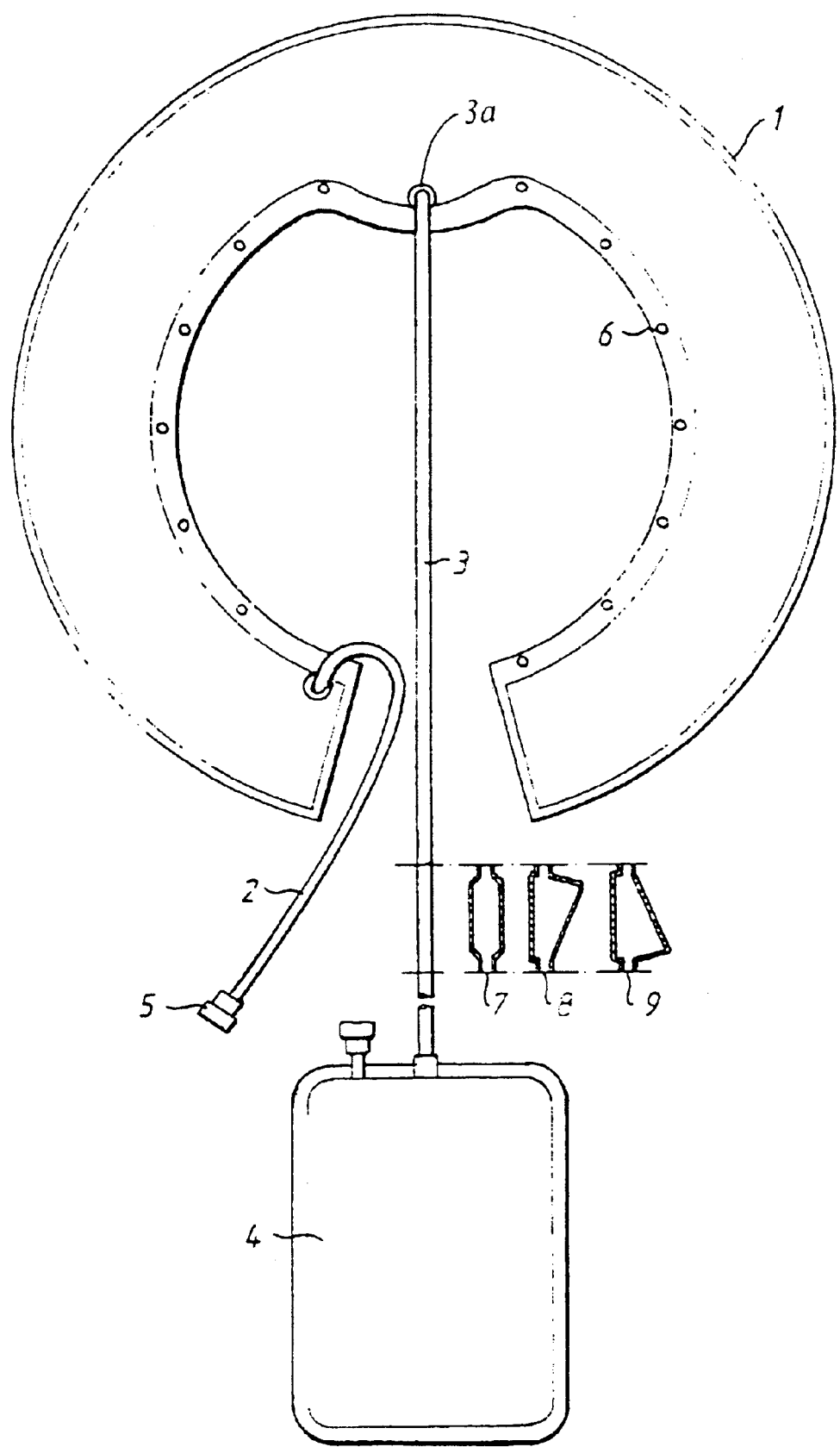
FIG. 1 is a schematic top view of a bag assembly according to the invention.

FIG. 1 shows a bag assembly intended for production of platelets from a pooled buffy coat. The bag assembly comprises an essentially annular processing bag 1, having an inlet tube 2 and an outlet tube 3 terminated by a platelet storage bag 4. The outlet tube is connected to an outlet 3a disposed at the radially inner portion of the processing bag. The annular processing bag 1 is in principle similar to the round bag disclosed in the above-mentioned EP-B1-0304 431, however, with a middle portion removed. The annular processing bag 1 is dimensioned and shaped for being placed in a centrifuge of a corresponding construction, also disclosed in said EP-B1-0304 431. The bag assembly is sterilized before use.

In accordance with the prior art principle of use, at least one buffy coat storage bag is connected to the first bag 1 via inlet tube 2, and the buffy coat in said storage bag is transferred to said processing bag 1. Preferably, the content of several such buffy coat bags, such as six bags, is transferred to the processing bag, dependent on the relative size of said bags.

The connection can take place by a sterile connecting method known in the art, such as shown in for example EP-A3-0 508 474. Otherwise, such connection can take place by sterile connectors 5, one of which is shown in FIG. 1. The exact way of transferring the buffy coat to the processing bag is not the object of the present invention and is not further described here.

Then, the inlet tube 2 is closed and the processing bag 1 is placed in a centrifuge and processed for a predetermined time in a predetermined G-field.

Finally, the light-weight fraction of the content of the processing bag, which is plasma enriched with thrombocytes, is transferred to the platelet storage bag 4 via the outlet tube 3, which normally comprises a cell filter, such as a filter for leucocytes, and the outlet tube is sealed and cut to provide the separated platelets in the storage bag 4. The remaining content of the processing bag is usually discarded.

According to the present invention, the cell filter is replaced by a cell trap as described more closely below.

Figure 2:
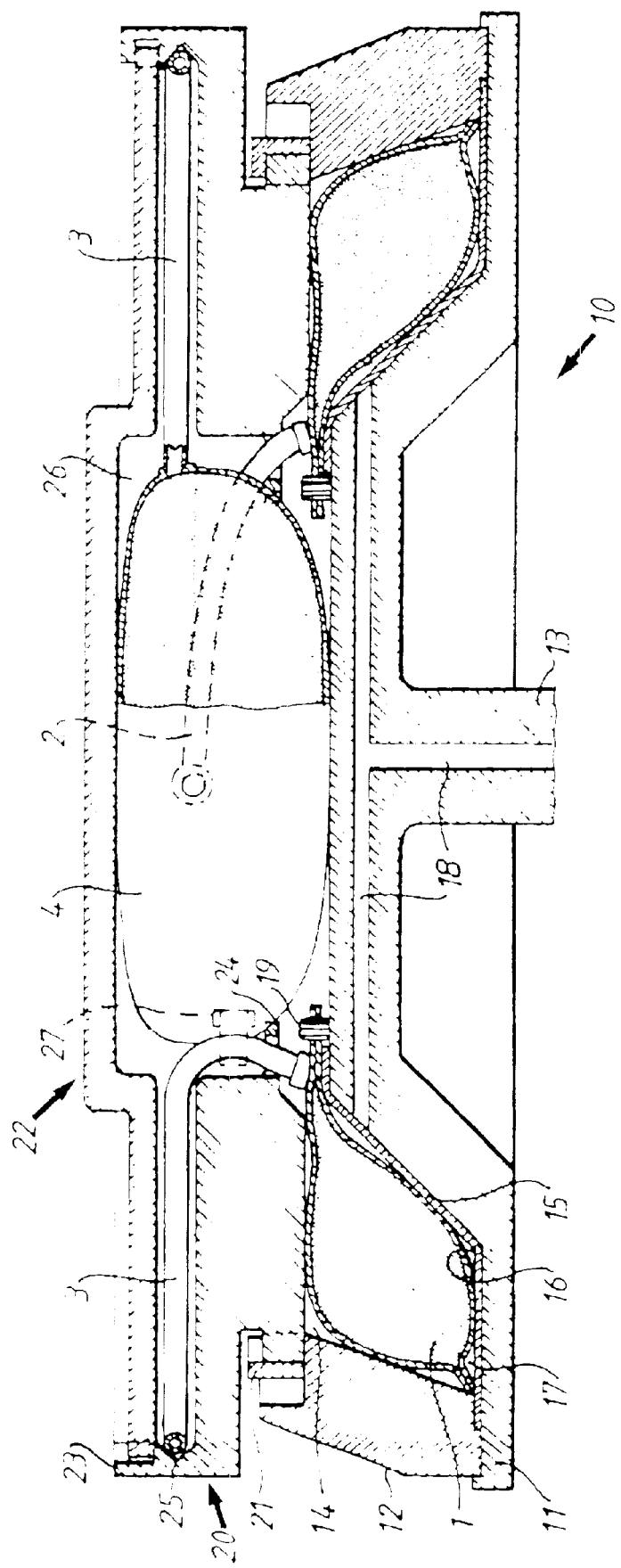
FIG. 2 is a cross-sectional view of a centrifuge rotor together with the bag assembly of FIG. 1.

A centrifuge rotor suitable for performing such a separation is shown in FIG. 2. The centrifuge rotor 10 comprises a centrifuge rotor plate 11 of the design shown in FIG. 2. At the periphery of the rotor plate 11, there is attached a ring 12, delimiting an annular, conically depending pocket 14. The rotor plate 11 and the ring 12 are supported by a shaft 13 and are rotatable as a unit at a desired rotation speed by a motor (not shown).

The plate is provided with a membrane 15, which covers the bottom surface 16 of the annular depending pocket 14. The membrane is attached to the bottom surface at the inner periphery and the outer periphery of the membrane via a suitable adhesive or in another appropriate way. Then, there is formed a space 17 between the bottom surface 16 and the membrane which space is closed at the inner and outer periphery. Said space 17 is connected to a tube 18 extending via the shaft 13 to a rotational coupling and to a fluid source. By exerting a fluid pressure via said fluid source and said tube 18 inside said space 17, the membrane can expand upwards in FIG. 2 as further explained below.

The rotor plate 11 is provided with small studs 19 arranged in a ring close to the inner periphery of said membrane. The annular processing bag 1 is provided with several holes 6, which can engage said studs 19 as shown in FIG. 2 to place the bag 1 in position in the pocket 14 as shown.

Moreover, the centrifuge rotor 10 comprises a closure portion 20 which can be placed on the upper surface of the ring 12 and be maintained in position via locking members 21, similar to a bayonet lock. The closure portion 20 comprises a removable lid portion 22, which is attached to the closure portion 20 via locking members 23 similar to locking members 21.

Closure member 20 comprises a ring portion 24, which in the assembled position prevents the bag from becoming free from the studs 19 as shown in FIG. 2.

Closure member 20 further comprises a ring groove 25 close to the outer periphery as shown in FIG. 2. The ring groove 25 is adapted to enclose the outlet tube 3 of the bag assembly and place the outlet tube 3 at a radial distance from the shaft 13, which is the same or even greater than the processing bag 1. The outlet tube 3 has a length sufficient for encircling the processing bag 1 by approximately half a turn of one revolution. Thus, the outlet tube 3 has a length which is equal to half the circumference of the processing bag 1 plus some extra portions for the radial extensions. It is possible to use a very short peripheral portion and using mainly the radial portions for the cell trap operation, as well as a peripheral portion which has one revolution or more.

Closure portion 20 encircles a central space 26, in which the platelet storage bag 4 is placed as well as the inlet tube 2. The lid portion 22 covers the central space 26 so that the content of the centrifuge rotor cannot escape during centrifugation.

The centrifuge rotor 10 is assembled as shown in FIG. 2 at the initiation of a centrifuge process. The lid portion 22 is removed and the inlet tube 2 is connected to a number of buffy coat bags and the contents thereof are transferred to the annular processing bag 1 positioned in the depending pocket 14. The outlet tube 3 can be closed by a clamp 27 (shown by broken lines) so that no buffy coat can enter outlet tube 3 by mistake. The transfer of the buffy coat to the processing bag can also take place in advance, so that the bag assembly is loaded in the centrifuge already provided with buffy coat to be treated.

Then, the clamp 27 is removed and the lid portion 22 is closed and the centrifuge is rotated to separate the contents of the processing bag 1 into a light-weight fraction enriched with platelets and a remainder comprising erythrocytes, leukocytes and other high density cells. Such centrifugation takes place at a predetermined G-field during a predetermined time, which is conventionally determined. There is no risk that buffy coat will enter outlet tube 3 during this process, since there is always enough space in the processing bag for the buffy coat.

When the centrifugation step is completed, the membrane 15 is activated and fluid is introduced in space 17 below the membrane via tube 18, while the centrifuge is still rotating at the same speed, or alternatively at a slower speed. The membrane 15 urges the bag 1 towards the bottom portion of closure portion 20 so that the volume of the bag is decreased and the content thereof is passed to the outlet tube 3. It is the light-weight fraction enriched with platelets that reaches the outlet tube 3 first since membrane 15 exerts a G-force balanced pressure on the outside of bag 1.

The enriched portion enters outlet tube 3 and passes radially outwards along the tube to the tube portion positioned in the groove 25 and along the periphery of the groove and then finally radially inwards to the storage bag 4. The storage bag 4 is initially collapsed, i.e., without any considerable amount of air or gas inside it. When a predetermined amount of fluid has been pumped into the space 17 under the membrane 15, the separation process is terminated and the centrifuge is stopped and the storage bag is separated from the processing bag. The storage bag is closed and stored for subsequent use while the remaining bag and tubes are discarded.

The outlet tube 3 acts as a cell filter, since the heavier cells, such as red and white blood cells, under the influence of the G-field, tend to accumulate and attach to the outer surface of the tube and do not follow the fluid flow, bringing with it only the platelets. Thus, the outlet tube 3 forms a cell trap eliminating the need for using a separate cell filter as in the prior art. It is the positioning of the outlet tube 3 at a high G-field that makes it possible to use it as a cell trap.

The cell trapping ability can be improved by adding an enlargement at a suitable position along the outlet tube. Three different embodiments of such enlargements 7,8 and 9 are shown in FIG. 1 and are intended to be incorporated in the outlet tube 3 as indicated.

Such an enlargement can be arranged where the radial flow in the beginning of outlet tube is linked into a peripheral flow when tube 3 enters the groove 25. Another convenient position is when the outlet tube exits the groove 25 and extends radially inwards. Of course, several cell trap enlargements can be arranged along the outlet tube.

Figure 3:
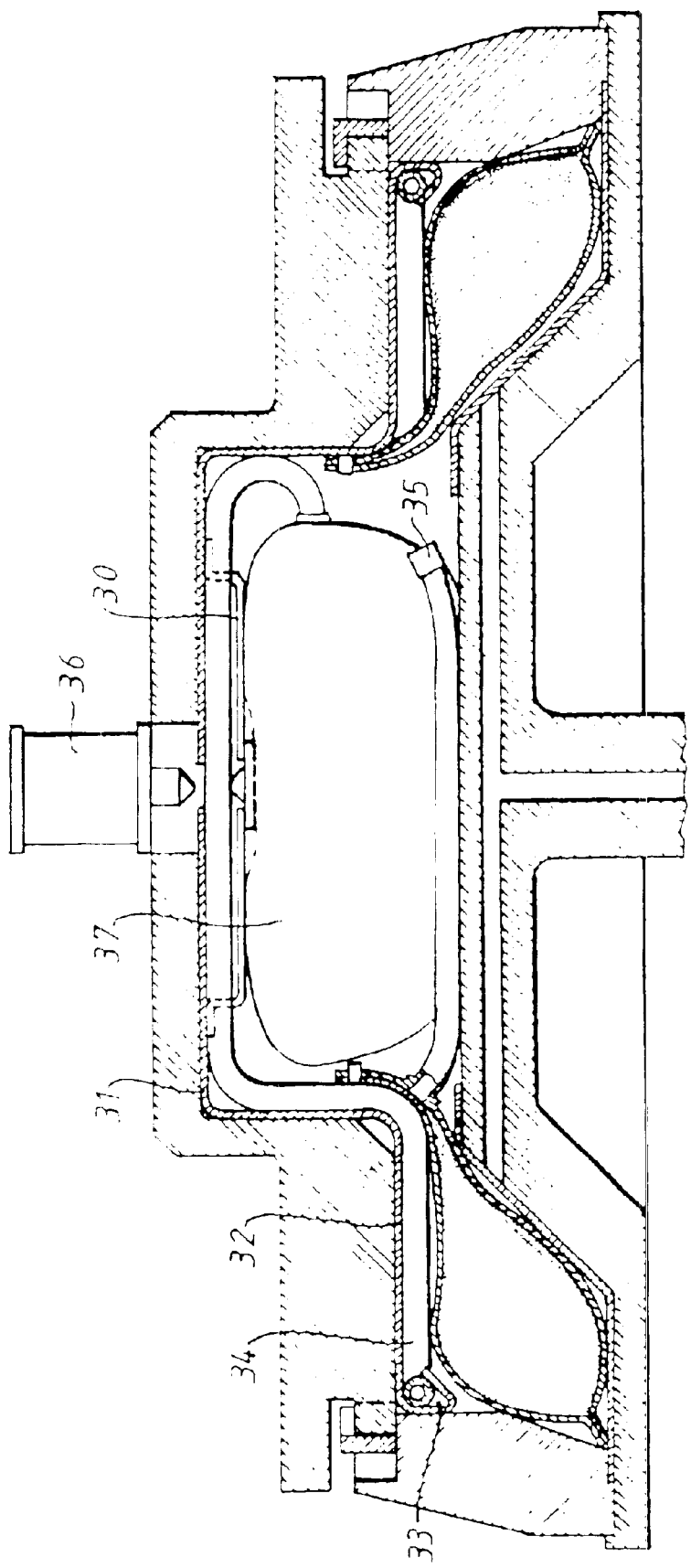
FIG. 3 is a cross-sectional view similar to FIG. 2 of an alternative embodiment of the invention.

In FIG. 3 there is shown another embodiment of the centrifuge and the bag assembly according to the invention. In this embodiment, a central portion of the ring bag is used as the platelet storage bag. The bag assembly is arranged with an insert 30 already at the manufacturing step. The insert 30 has a shape which closely follows the interior of the closure portion 20. Thus, the insert and the bag assembly can be placed in the rotor and the closure portion can be attached, and the centrifuge is ready for operation.

The insert 30 has the same configuration as the insert in the prior art patent specification WO 95/01842 mentioned above. The insert 30 has a generally cup-shaped central portion 31 and a ring-shaped outer portion 32. The ring-shaped outer portion 32 comprises a peripheral groove 33 similar to groove 25 and enclosing the outlet tube 34.

This embodiment of the bag assembly is preferably filled with buffy coat before being placed in the centrifuge. Such filling takes place via an inlet tube 35, which is then closed and sealed.

The outlet tube 34 passes a magnetic valve 36, which closes and opens the outlet tube 34 at initiation of the filling step and ends in a storage bag 37.

Figure 4:
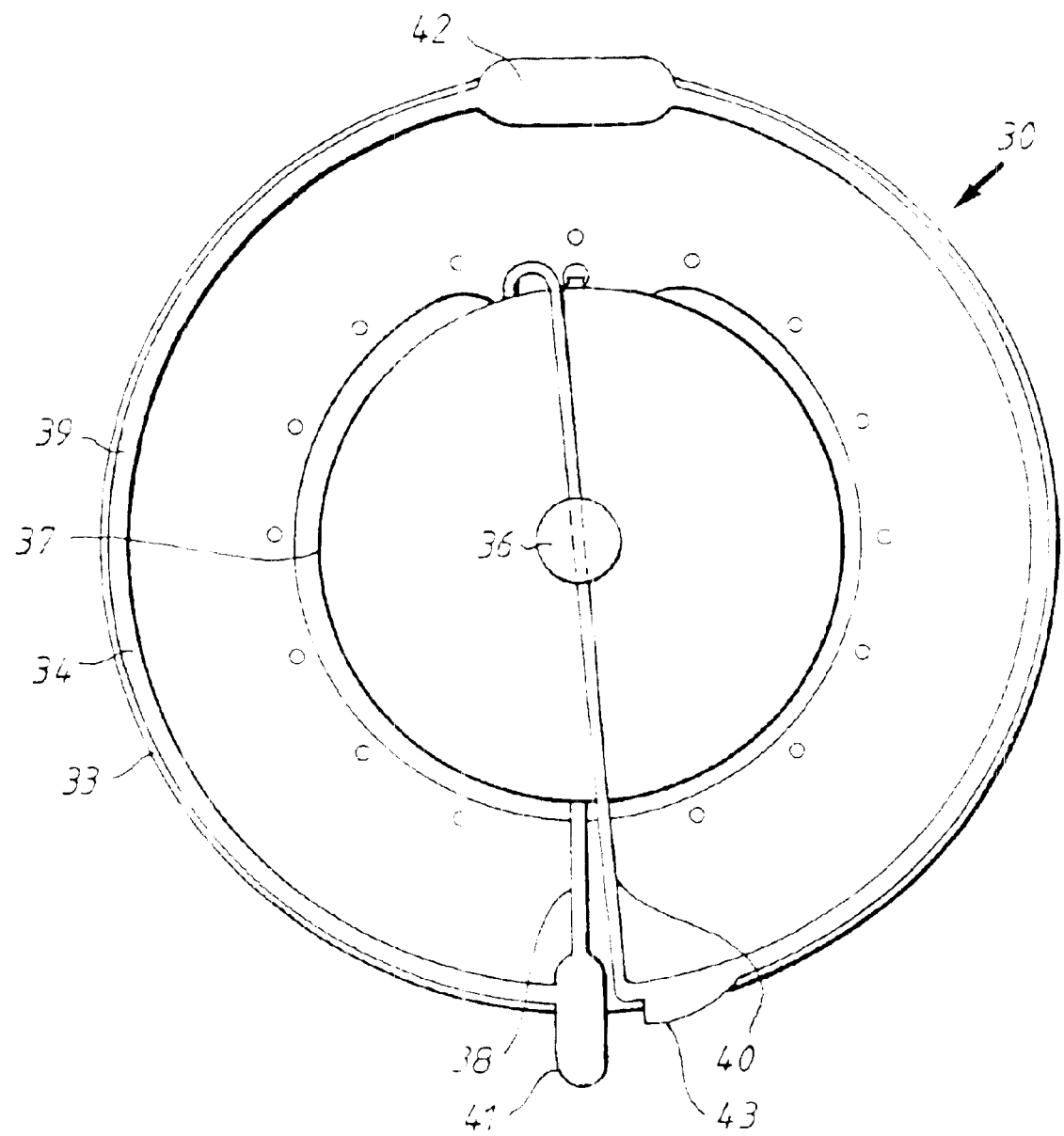
FIG. 4 is a top view of an insert provided with a bag assembly of FIG. 1.

The operation of the embodiment shown in FIG. 3 is similar to the operation of the embodiment shown in FIG. 2 and need not be further described. The use of an insert for maintaining the bag assembly in a specific position makes it easier to operate the bag assembly and makes it more safe. FIG. 4 shows the insert 30 from below provided with the storage bag 37 in the central cup-shaped portion and the outlet tube 34 placed in a peripheral groove. For clarity, the annular processing bag is removed.

The outlet tube 34 has a first radial portion 38 extending radially outwards to the periphery. Then, the outlet tube 34 includes a central peripheral portion 39 extending almost one revolution along the periphery. Finally, the outlet tube 34 is terminated by a radial portion 40 extending inwards from the periphery and to the valve member 36 positioned centrally in the insert, and then to the inlet of the storage bag 37.

As clearly shown in FIG. 4, the outlet tube 34 comprises one or several enlargements or cell traps 41, 42, 43.

A first type of chamber or cell trap 41 is shown between the first radial portion 38 and the peripheral portion 39. The cell trap extends radially and has a side connection to the peripheral portion 39. The heavier cells having a flow speed in the radial direction continue straight ahead into the cell trap vessel, while the light-weight fraction is deviated to the peripheral portion 39.

A second type of chamber or cell trap 42 is shown at the middle of the peripheral portion 39 but can be placed anywhere along the length of the outlet tube. The cell trap 42 is in principle an enlargement of the tube, where the heavier cells can be maintained. The flow speed in the enlargement is slower which means that the heavier cells will be forced outwards by the G-field and maintained in the cell trap. The cell trap can include some material having an affinity towards erythrocytes and leukocytes. The material is attached to the wall of the cell trap so that such cells are maintained in the cell trap when forced towards the wall having such material.

A third type of chamber or cell trap 43 is shown at the end close to the radial portion 40. Cell trap 43 is in principle only an enlargement of cell trap 42, but has a shape and dimension suitable for maintaining such cells as desired. The space outside the flow path can be provided with some type of absorption material as described above.

In FIG. 4, the outlet tube 34 and the cell traps 41, 42, 43 are positioned at the same or close to the same radial distance as the outer edge of the processing bag.

By using one or several of the cell traps shown above, a specific cell filter can be avoided in relation to prior art. Such cell filters are expensive. Thus, the cell trap according to the present invention provides an economic advantage while maintaining a high separation capacity.

Another way of forming a cell trap is shown in more detail in FIG. 5. The round bag assembly 50 is divided in two portions by an annular weld 51 provided on the round bag as shown in FIG. 5. The first inner portion 52 is the processing bag proper where the separation takes place, and the outer portion 53 forms a cell trap according to the present invention.

The processing inner portion 52 is filled with buffy coat via an inlet tube 54 as described above. The inlet tube 54 is then closed, for example heat sealed.

After centrifugation, there is exerted a pressure on the inner bag portion 52, whereby the content thereof is transferred via an outlet tube 55 to the inner portion at one side thereof and then, along the entire periphery of the outer bag portion to the other end thereof and then to a storage bag. Thus, the outer bag portion 53 operates as a cell trap.

In FIG. 6 there is shown an insert 60 for retaining the bag assembly 50 according to FIG. 5 in position. The different portions of the bag assembly are attached to the insert via adhesive pads 61 as shown to the left in the figure. As appears from FIGS. 5 and 6, the different portions of the bag assembly are manufactured in one step from two or three sheets of plastic material and provided with separation and sealing weldings at desired positions in one and the same step. Thus, the bag assembly is very inexpensive to manufacture. The bag assembly is then divided in its separate parts and mounted to an insert to maintain integrity during subsequent transport and handling.

Figure 7:
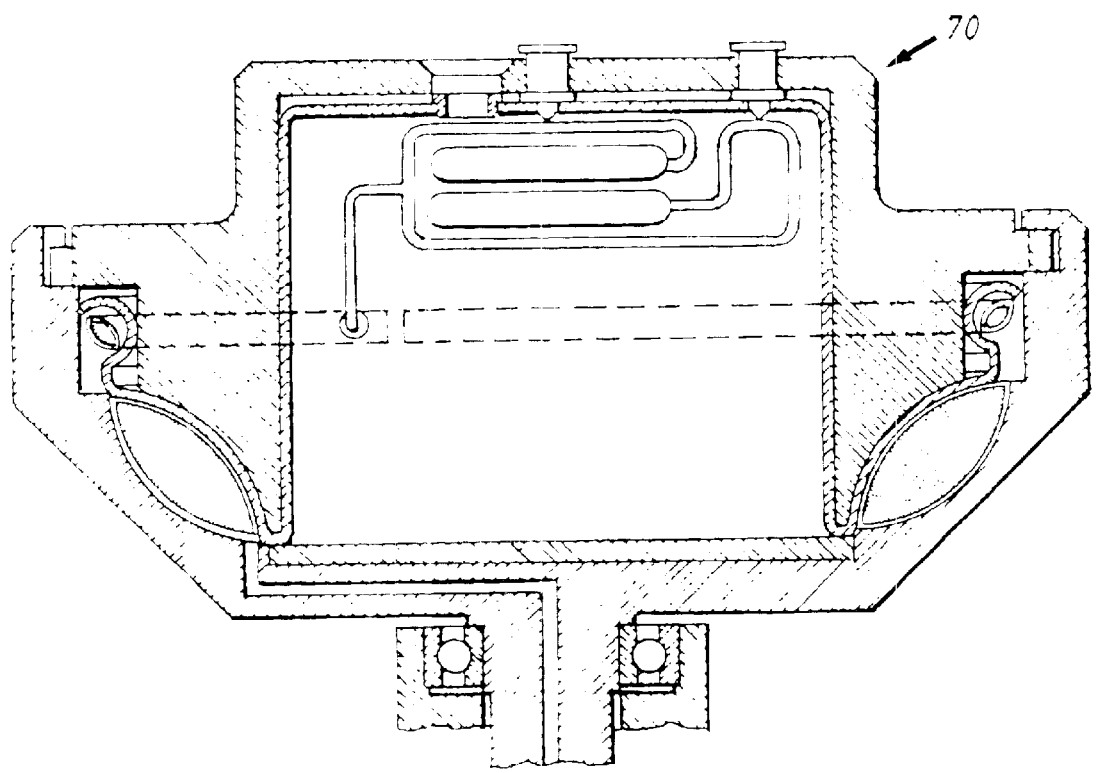
FIG. 7 is a cross-sectional view of a centrifuge rotor provided with the insert according to FIG. 6 and a bag assembly according to FIG. 5.

The insert is placed in a centrifuge rotor 70 as shown in FIG. 7. The operation of the centrifuge is similar to that described above, and need not be further described. However, the annular processing bag has an inclination in another direction compared to FIG. 3 as is evident from FIG. 7.

Turning back to FIG. 5, there is shown by broken lines 56 that the outer periphery of the outer bag portion 53 can be provided with a sinuous outer borderline. This borderline will generate spaces 57 with stagnant flow, where more dense cells can accumulate. Once trapped in such a space 57, the heavier cells, leucocytes, will remain therein, while the lighter cells, platelets, will follow the flow of plasma. Generally, leucocytes have a tendency to attach to the wall surface of the plastic material, which further aids the separation. It is of importance that the radially inner borderline of the outer bag portion 53 is smooth and has no discontinuities, so that the flow of plasma and platelets can take place without any hindrance.

The cell trap according to the invention can also be arranged without any peripheral portion and only use the feature that the flow in the outlet tube 3 first is radially outwards and then changes the direction 180° and continues radially inwards. The heavier cells, leukocytes, will have difficulty to follow such a change of direction and the lighter cells, platelets, will follow the flow. Thus, a separation will take place. Such an embodiment can be obtained from FIG. 4 by combining chambers 41 and 43 to a single chamber and excluding the peripheral tube 34, 39 etc.

Another more elaborate embodiment is shown in FIG. 8. The bag assembly 80 comprises a nearly annular processing bag 81, an outlet tube 83 and a platelet storage bag 84. The cell trap according to the invention comprises a first radial tube portion 85 followed by a chamber 86 and ended by a connection tube 87 to the platelet storage bag 84. The chamber 86 is made from the material between the ends of the nearly annular processing bag 81 as appears from FIG. 8. To the left of the symmetry line is shown a triangular shape 89 and to the right of the symmetry line is shown a more rectangular shape 88. Preferably, the chamber 86 is symmetrical.

In FIG. 9 there is shown a centrifuge rotor 90 provided with the bag assembly 80 of FIG. 8 arranged at an insert 82. As in the embodiment of FIG. 2, the rotor cover is made up of two separate portions 91 and 92. Between the two portions 91 and 92, there is arranged a recess 93 suitable for enclosing the chamber 86, as shown in FIG. 10A, where the chamber 86 is placed in position in the recess in an empty, collapsed condition. As appears from FIG. 9, the recess 93 has a complementary shape to the chamber 86, so that, when the chamber 86 is filled with liquid, the recess 93 supports the chamber, as shown in FIG. 10B.

The operation of the embodiment according to FIG. 8 and 9 is similar to the previous embodiments. The buffy coat is introduced in the processing bag 81 and the bag assembly 80 is placed inside the rotor centrifuge in an annular chamber 94, and the separation process is performed. After separation, a magnetic valve 95 opens the outlet tube 83 and the separated fraction is given off via the outlet tube 83 to the end of chamber 86 via the radial tube portion 85. Then, the fraction flows radially inward through chamber 86 under the influence of a G-field while the rotor is still rotating. The more dense cells are separated and the less dense cells follow the fraction and are given off to the storage bag 84.

The rotor cover portions 91 and 92 are provided with guide pins 97 and corresponding holes so that the mutual relationship between the two portions are always obtained. This will ensure that the recess 93 will always be formed between the two cover portions.

The upper walls of the chamber 86 (seen according to FIG. 8) are preferably inclined as shown in FIG. 8 to form a funnel-like outlet portion.

As appears from FIG. 9, outlet tube 83 and connection tube 87 are placed in a recess 96 in one of the cover portions 91 at the periphery thereof.

As is clear from the above description, the bag assembly 80 is placed in an insert 82 of a shape corresponding to the bag assembly and the rotor construction. Thus, the bag assembly can easily and conveniently be placed in the correct position in the rotor and the cover portions can be placed in position. As previously, the bag assembly is maintained to the insert by adhesive tapes arranged at necessary positions. The tube portions are placed in channels preformed in the insert. The insert is preferably made by a vacuum molding process.

It is possible to use the invention for separating other types of cells, such as stem cells. Stem cells are also included in the buffy coat and will be separated during the centrifugation. In this case, it is necessary to first remove the transparent fraction which essentially includes plasma, platelets and leucocytes. When the fraction turns red, the first light cells are stem cells.

For obtaining stem cells, it is necessary to include two collection bags attached to the outlet or connection tube, one 58 for taking care of the transparent fraction, and one 59 for the stem cell fraction. Moreover, the centrifuge comprises two magnetically operated valves 68, 69 one for each collection bag. The insert and the centrifuge rotor includes a window 67 through which the outlet tube portion connected to the first collection bag 58 is visible. When it is determined that the content of said outlet tube portion becomes red, this is an indication that the stem cell portion has reached this position, and the magnetic valves are reversed so that the outlet flow is directed to the other collection bag 59 for collection of stem cells. The collection continues until a predetermined volume has been collected, whereupon the process is terminated. Such a volume can be about 50 ml for a buffy coat volume of 500 ml. When such a volume has been collected it has been determined that the stem cell suspension is optimally enriched. There is no possibility to determine when the stem cells are followed by red blood cells, erythrocytes, since there is no significant color difference between these two types of cells.

During the process of obtaining stem cells it is of great importance not to use too high an outlet flow, since this flow will disturb the separation in the processing bag. A higher outlet flow can be used in the initial flow of transparent fraction since this fraction is discarded. Of course, it is possible to first collect the platelet enriched fraction, then discard the leucocyte fraction, and finally collect the stem cell fraction. This operation will require three collection bags.

Of course, it is convenient to use the spare material at the middle of the annular processing bag for forming the collection bag for the leukocyte fraction, since it is otherwise only discarded. The material in the collection bags is determined according to the intended use and is any conventional material used for such purpose. The material in the processing bag is PVC or similar material.

The invention has been described above with reference to specific embodiments of the invention. However, the different features of the embodiments can be combined in different manners and such combinations should be included within the scope of the invention. The invention is only limited by the appended patent claims.

What is claimed is:

1. A method of separating cells in a centrifuge comprising:
   providing a cell suspension in a processing bag connected via an outlet tube to a storage bag;
   separating the cell suspension in the processing bag into fractions by centrifugation in a centrifuge, at least one such fraction being enriched with specific cells;
   opening a centrifuge valve associated with said tube so as to allow a flow of fluid therethrough;
   transferring one of said fractions to the storage bag via the outlet tube;
   separating more dense cells from said fraction through at least one cell trap enlargement connected to said outlet tube;
   whereby said processing bag, said storage bag, said outlet tube and said centrifuge valve are all disposed in the rotating part of the centrifuge during centrifugation.

2. A method according to claim 1 in which said cell suspension includes a buffy coat and said enriched fraction is a light-weight fraction enriched with platelets.

3. A method according to claim 1 in which the transferring of said fraction via said outlet tube includes flowing through said valve and through a radially positioned portion of said outlet tube having a radially outwardly directed flow.

4. A method according to claim 1 in which said cells are platelets or stem cells.

5. A method according to claim 1 in which said cells are red blood cells.

6. A method according to claim 1 in which said valve is a manually activatable clamp.

7. A method according to claim 1 in which said valve is a magnetically activatable valve.

8. A method according to claim 1 in which said valve is an electromagnetically activatable valve.

9. A method of separating cells in a centrifuge comprising:
   providing a cell suspension in a process bag connected via an outlet rube to a storage bag;
   adapting said outlet tube in a position having a radially inwardly directed flow and having a centrifuge valve associated therewith;

separating the cell suspension in the processing bag into fractions by centrifugation in a centrifuge, at least one such fraction being enriched with specific cells;

opening the centrifuge valve associated with said tube so as to allow a flow of fluid therethrough;

transferring one of said fractions to the storage bag via the outlet tube;

diverting said radial flow into a peripheral flow via a cell trap having an enlarged section for maintaining specific cells, whereby said processing bag, said storage bag, said outlet tube and said centrifuge valve are all disposed in the rotating part of the centrifuge during centrifugation.

* * * * *